(12) United States Patent
Sakamoto et al.

(10) Patent No.: US 9,918,465 B2
(45) Date of Patent: *Mar. 20, 2018

(54) METHOD FOR REDUCING DAMAGE BY HARMFUL ORGANISMS IN CORN CULTIVATION

(71) Applicant: SUMITOMO CHEMICAL COMPANY, LIMITED, Tokyo (JP)

(72) Inventors: Norihisa Sakamoto, Kasai (JP); Mayuko Ozawa, Takarazuka (JP); Atsushi Iwata, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/229,807

(22) Filed: Aug. 5, 2016

(65) Prior Publication Data

US 2016/0338349 A1 Nov. 24, 2016

Related U.S. Application Data

(62) Division of application No. 13/944,367, filed on Jul. 17, 2013, now Pat. No. 9,439,415.

(30) Foreign Application Priority Data

Jul. 20, 2012 (JP) ................................. 2012-161340

(51) Int. Cl.
| | |
|---|---|
| *A01B 49/06* | (2006.01) |
| *A01C 7/06* | (2006.01) |
| *A01C 7/08* | (2006.01) |
| *A01G 1/00* | (2006.01) |
| *A01N 25/00* | (2006.01) |
| *A01N 25/12* | (2006.01) |
| *A01N 37/34* | (2006.01) |
| *A01N 37/36* | (2006.01) |
| *A01N 43/80* | (2006.01) |
| *A01N 25/04* | (2006.01) |
| *A01N 47/36* | (2006.01) |
| *A01N 47/38* | (2006.01) |
| *A01N 51/00* | (2006.01) |
| *A01N 53/00* | (2006.01) |
| *C05B 17/00* | (2006.01) |
| *A01N 47/44* | (2006.01) |

(52) U.S. Cl.
CPC .............. *A01N 25/04* (2013.01); *A01B 49/06* (2013.01); *A01C 7/06* (2013.01); *A01C 7/081* (2013.01); *A01G 1/001* (2013.01); *A01N 25/00* (2013.01); *A01N 25/12* (2013.01); *A01N 37/34* (2013.01); *A01N 37/36* (2013.01); *A01N 43/80* (2013.01); *A01N 47/36* (2013.01); *A01N 47/38* (2013.01); *A01N 47/44* (2013.01); *A01N 51/00* (2013.01); *A01N 53/00* (2013.01); *C05B 17/00* (2013.01)

(58) Field of Classification Search
CPC ......... A01B 49/06; A01B 49/04; A01B 49/00; A01C 7/06; A01C 7/00; A01C 7/081; A01C 7/08; A01G 1/001; A01G 1/00; A01G 47/08; A01G 47/00; A01G 47/38; A01G 47/44; A01G 47/42; A01G 47/40; A01G 51/00; A01G 53/00; C05B 17/00
USPC .......... 111/118, 120, 121, 129, 14, 149, 157, 111/163–170, 174, 183–188, 200, 900; 239/34; 514/65, 355, 520
See application file for complete search history.

(56) References Cited

U.S. PATENT DOCUMENTS

| | | |
|---|---|---|
| 4,495,875 A | 1/1985 | Makkink |
| 6,426,082 B1 | 7/2002 | Ueda et al. |
| 6,553,925 B1 | 4/2003 | Beaujot |
| 9,439,415 B2 * | 9/2016 | Sakamoto .............. A01N 25/04 |
| 2005/0261129 A1 | 11/2005 | Dutcheshen |

(Continued)

FOREIGN PATENT DOCUMENTS

| | | |
|---|---|---|
| JP | 2013-133308 A | 7/2013 |
| JP | 2013-133309 A | 7/2013 |

(Continued)

OTHER PUBLICATIONS

2012 North Carolina Agricultural Chemicals Manual, Jan. 26, 2012, pp. 65, 70, 71, and 72 (http://www.nurserycropscience.info/ipm/chemical-persticides/extension-pubs/insect-control.pdf).

An English translation of the Hungarian Office Action issued in the corresponding Hungarian Patent Application No. P1300436 dated Mar. 13, 2015.

French Written Opinion and Preliminary Search Report, dated Nov. 21, 2014, for French Application No. 1357106, along with a partial English translation.

(Continued)

*Primary Examiner* — Christopher J. Novosad

(74) *Attorney, Agent, or Firm* — Birch, Stewart, Kolasch & Birch, LLP

(57) ABSTRACT

A method for reducing damage by harmful organisms in corn cultivation. Damage by harmful organisms in corn cultivation can be reduced by carrying out the steps of: A) making a furrow in a cultivated land; B) seeding the furrow formed in the foregoing step with corn; C) applying to the furrow one or more selected from Compound Group (II), or C') applying to the furrow one or more selected from Compound Group (I) and one or more selected from Compound Group (II); and D) closing the furrow. Compound Group (I): clothianidin, thiamethoxam, imidacloprid and thiacloprid; Compound Group (II): bifenthrin, bioresmethrin, deltamethrin, bioallethrin, ethofenprox, fenpropathrin, cypermethrin, alpha-cypermethrin, zeta-cypermethrin, fenvalerate, esfenvalerate, cyfluthrin, beta-cyfluthrin, alpha-cypermethrin, tralomethrin, fluvalinate, permethrin, lambda-cyhalothrin, flucythrinate and tefluthrin.

5 Claims, No Drawings

(56) References Cited

U.S. PATENT DOCUMENTS

| | | |
|---|---|---|
| 2006/0014724 A1 | 1/2006 | Jadhav et al. |
| 2011/0174898 A1 | 7/2011 | Peyron |
| 2011/0269625 A1 | 11/2011 | Andersch et al. |
| 2014/0020610 A1 | 1/2014 | Sakamoto et al. |

FOREIGN PATENT DOCUMENTS

| | | | |
|---|---|---|---|
| RU | 2142230 C1 * | 12/1999 | ............. A01N 53/00 |
| WO | WO 02/30201 A2 | 4/2002 | |
| WO | WO 02/30202 A2 | 4/2002 | |
| WO | WO 2010/007239 A2 | 1/2010 | |
| WO | WO 2010/022917 A2 | 3/2010 | |
| WO | WO 2012/059328 A2 | 5/2012 | |

OTHER PUBLICATIONS

Spanish Search Report and partial English translation thereof, dated Jan. 31, 2014, for Spanish Application No. 201331093.
Wright et al., "Corn Insect Management," Entomological Society of America, 1999, pp. 10-21 and 44-119, ISBN: 0-938522-76-0.
Christensen B, Derwent Acc-No. 2002-050183, Derwent Week: 200641, for Abstracted-Pub-No. DE 10058878A1, Pub-Date Sep. 30, 2001.
Gao B, Derwent Acc-No. 2011-F06947, Derwent Week: 201133, for Pub-No. CN 201781744, Pub-Date Apr. 6, 2011.
Office Action (including an English translation thereorf) issued in the corresponding French Patent Application No. 1357106 dated Oct. 23, 2015.

* cited by examiner

METHOD FOR REDUCING DAMAGE BY HARMFUL ORGANISMS IN CORN CULTIVATION

CROSS-REFERENCE TO RELATED APPLICATIONS

This application is a Divisional of co-pending application Ser. No. 13/944,367 filed on Jul. 17, 2013, which claims priority under 35 U.S.C. § 119(a) to Patent Application No. 2012-161340 filed in Japan on Jul. 20, 2012. All of the above applications are hereby expressly incorporated by reference into the present application.

BACKGROUND OF THE INVENTION

Field of the Invention

The present invention relates to a method for reducing damage by harmful organisms in corn cultivation.

Description of the Related Art

Previously, various methods have been known as a method for reducing damage by harmful organisms in corn cultivation.

PRIOR ART LITERATURE

Non-Patent Literature

Non-Patent Literature 1: Handbook of Corn Insects. ISBN: 0-938522-76-0., 1999. Entomological Society of America

SUMMARY OF THE INVENTION

In corn cultivation, with worldwide cereal demand expansion, various efforts have been made in order to increase a yield, but since a reduction in yield due to harmful organisms such as pests and weeds has been significant, development of a method for reducing damage by harmful organisms in corn cultivation has been desired.

The present inventors have conducted studies for finding out a method for reducing damage by harmful organisms in corn cultivation, and resultantly found out that damage by harmful organisms in corn cultivation can be reduced by carrying out the steps of: A) making a furrow in a cultivated land (hereinafter, referred to as step A in some cases); B) seeding with corn a furrow formed in the foregoing step (hereinafter, referred to as step B in some cases); C) applying to the furrow one or more selected from the below-mentioned compound group (II) (hereinafter, referred to as the present compound (II) in some cases) (hereinafter, referred to as step C in some cases); and D) closing the furrow (hereinafter, referred to as step D in some cases).

The present inventors have also conducted studies for finding out a method for reducing damage by harmful organisms in corn cultivation, and resultantly found out that damage by harmful organisms in corn cultivation can be reduced by carrying out the steps of: A) making a furrow in a cultivated land (hereinafter, referred to as step A in some cases); B) seeding with corn a furrow formed in the foregoing step (hereinafter, referred to as step B in some cases); C') applying to the furrow one or more selected from the below-mentioned compound group (I) (hereinafter, referred to as the present compound (I) in some cases) and one or more selected from the below-mentioned compound group (II) (hereinafter, referred to as the present compound (II) in some cases) (hereinafter, referred to as step C' in some cases); and D) closing the furrow (hereinafter, referred to as step D in some cases).

That is, the present invention is as follows:

[1] A method for reducing damage by harmful organisms in corn cultivation, the method comprising the steps of:
A) making furrow in a cultivated land; B) seeding with corn a furrow formed in the foregoing step; C) applying to the furrow one or more selected from the below-mentioned compound group (II); and D) closing the furrow.
(compound group (II): group consisting of bifenthrin, bioresmethrin, deltamethrin, bioallethrin, ethofenprox, fenpropathrin, cypermethrin, alpha-cypermethrin, zeta-cypermethrin, fenvalerate, esfenvalerate, cyfluthrin, beta-cyfluthrin, alpha-cypermethrin, tralomethrin, fluvalinate, permethrin, lambda-cyhalothrin, flucythrinate and tefluthrin)

[2] The method according to [1], wherein the step of applying one or more selected from the compound group (II) is a step of applying a composition containing one or more selected from the compound group (II).

[3] The method according to [2], wherein the composition containing one or more selected from the compound group (II) is a granule or micro-granule containing one or more selected from the compound group (II).

[4] The method according to [2], wherein the composition containing one or more selected from the compound group (II) is an aqueous dispersion or aqueous solution containing one or more selected from the compound group (II).

[5] The method according [4], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (II).

[6] A method for reducing damage by harmful organisms in corn cultivation, the method including the steps of:
A) making a furrow in a cultivated land; B) seeding with corn a furrow formed in the foregoing step; C') applying to the furrow one or more selected from the below-mentioned compound group (I) and one or more selected from the below-mentioned compound group (II); and D) closing the furrow.
(compound group (I): group consisting of clothianidin, thiamethoxam, imidacloprid and thiacloprid;
compound group (II): group consisting of bifenthrin, bioresmethrin, deltamethrin, bioallethrin, ethofenprox, fenpropathrin, cypermethrin, alpha-cypermethrin, zeta-cypermethrin, fenvalerate, esfenvalerate, cyfluthrin, beta-cyfluthrin, alpha-cypermethrin, tralomethrin, fluvalinate, permethrin, lambda-cyhalothrin, flucythrinate and tefluthrin)

[7] The method according to [6], wherein the step of applying one or more selected from the compound group (I) and one or more selected from the compound group (II) is a step of applying a composition containing one or more selected from the compound group (I) and a composition containing one or more selected from the compound group (II).

[8] The method according to [7], wherein the composition containing one or more selected from the compound group (I) is a granule or micro-granule containing one or more selected from the compound group (I).

[9] The method according to [7], wherein the composition containing one or more selected from the compound group (I) is an aqueous dispersion or aqueous solution containing one or more selected from the compound group (I).

[10] The method according to any one of [7] to [9], wherein the composition containing one or more selected from the compound group (II) is a granule or micro-granule containing one or more selected from the compound group (II).

[11] The method according to any one of [7] to [9], wherein the composition containing one or more selected from the compound group (II) is an aqueous dispersion or aqueous solution containing one or more selected from the compound group (II).

[12] The method according to [9], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I).

[13] The method according to [11], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (II).

[14] The method according to [6], wherein the step of applying one or more selected from the compound group (I) and one or more selected from the compound group (II) is a step of applying a composition containing one or more selected from the compound group (I) and one or more selected from the compound group (II).

[15] The method according to [14], wherein the composition containing one or more selected from the compound group (I) and one or more selected from the compound group (II) is a granule or micro-granule containing one or more selected from the compound group (I) and one or more selected from the compound group (II).

[16] The method according to [14], wherein the composition containing one or more selected from the compound group (I) and one or more selected from the compound group (II) is an aqueous dispersion or aqueous solution containing one or more selected from the compound group (I) and one or more selected from the compound group (II).

[17] The method according to [16], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I) and one or more selected from the compound group (II).

[18] The method according to any one of [1] to [17], wherein the land is ditched to a depth of 1 to 10 cm.

[19] The method according to any one of [1] to [18], wherein making furrow is performed using a disk furrow opener.

[20] The method according to any one of [1] to [19], wherein seeding is performed using a pneumatic seeder.

According to the present invention, harmful organisms in corn cultivation can be prevented, therefore, damage by harmful organisms in corn cultivation can be reduced.

DETAILED DESCRIPTION OF THE PREFERRED EMBODIMENTS

For the order of carrying out steps, usually, a step A, and then steps B and C or C' are carried out. In the step A, usually, a furrow having a V-shaped cross section is formed in a linear shape on a cultivated land. The step A may be carried out, followed by carrying out the step B, and then the step C or C', or the order may be reversed. The steps B and C or C' may be carried out in parallel. Usually, a step D is carried out after the steps B and C or C'.

In the present invention, usually, a seeder which is pulled with a tractor is used. Examples of the seeder include a composite-type seeder including a ditching part for forming a furrow, a seeding part for seeding a furrow in a speed linkage manner through piping from a hopper box filled with a seed, an agricultural chemical application parts for applying the present compound (II) or an agricultural chemical application part for applying the present compound (I) and the present compound (II) aqueous solution in a speed linkage manner through piping from one or more reservoirs filled with the present compound (I) and the present compound (II) collectively or separately, a furrow closing part for closing the furrow by gathering together a soil on the side of the formed furrow, and so on.

The ditching part of a seeder is usually attached to a front part of the seeder, and a furrow is formed on a cultivated land with movement of a tractor. Examples of the ditching part include a ploughshare furrow opener and a disk furrow opener, and a ditching system using a disk furrow opener which has a strong force of cutting a crop residue, has a small reduction in a cutting force due to adhesion of a soil, and can stabilize the depth of a furrow is preferable in that a furrow can be seeded and a chemical can be applied to the furrow uniformly due to stabilization of a depth of a furrow, so that the effect of the chemical is stabilized.

The depth of the furrow formed on a cultivated land can be appropriately changed depending on the soil condition of a place of corn cultivation, the condition of cultivating corn thereafter, and the weather condition, and is usually 1 to 10 cm, preferably 2 to 8 cm, further preferably 2 to 6 cm.

The seeding part of the seeder is usually attached to a rear of the ditching part, and the furrow is seeded with movement of a tractor. Examples of the seeding part include a mechanical seeder and a pneumatic seeder, and the pneumatic seeder using air pressure is preferable in that seed clogging or seeding leakage is small, so that seeding is stablyperformed, and a seed can be seeded in a furrow orderly. Examples of the pneumatic seeder include a vacuum suction type seeder and a blowing type seeder, and based on the reason of imparting little damage to a seed, a vacuum suction type seeder is preferable.

In the present invention when the present compound (II) is used, tefluthrin, bifenthrin, esfenvalerate, fenpropathrin, lambda-cyhalothrin or alpha-cypermethrin is preferable as the present compound (II). In the present invention when the present compound (I) and the present compound (II) are used, clothianidin, thiamethoxam or imidacloprid is preferable as the present compound (I), and tefluthrin, bifenthrin, esfenvalerate, fenpropathrin, lambda-cyhalothrin or alpha-cypermethrin is preferable as the present compound (II).

Clothianidin is a known compound, and is described in, for example, "The Pesticide Manual—15$^{th}$ edition (published by BCPC); ISBN 978-1-901396-18-8", page 229. This compound is obtained from a commercially available preparation, or is obtained by production through a known method.

Thiamethoxam is a known compound, and is described in, for example, "The Pesticide Manual—15th edition (published by BCPC); ISBN 978-1-901396-18-8". page 1112. This compound is obtained from a commercially available preparation, or is obtained by production through a known method.

Imidacloprid is a known compound, and is described in, for example, "The Pesticide Manual—15th edition (published by BCPC); ISBN 978-1-901396-18-8", page 645. This compound is obtained from a commercially available preparation, or is obtained by production through a known method.

Thiacloprid is a known compound, and is described in, for example, "The Pesticide Manual—15th edition (published by BCPC); ISBN 978-1-901396-18-8", page 1111. This compound is obtained from a commercially available preparation, or is obtained by production through a known method.

Tefluthrin is a known compound, and is described in, for example, "The Pesticide Manual—15th edition (published by BCPC); ISBN 978-1-901396-18-8", page 1083. This compound is obtained from a commercially available preparation, or is obtained by production through a known method.

Bifenthrin is a known compound, and is described in, for example, "The Pesticide Manual—15th edition (published by BCPC); ISBN 978-1-901396-18-8", page 1083. This compound is obtained from a commercially available preparation, or is obtained by production through a known method.

Esfenvalerate is a known compound, and is described in, for example, "The Pesticide Manual—15th edition (published by BCPC); ISBN 978-1-901396-18-8", page 433. This compound is obtained from a commercially available preparation, or is obtained by production through a known method.

Fenpropathrin is a known compound, and is described in, for example, "The Pesticide Manual—15th edition (published by BCPC); ISBN 978-1-901396-18-8", page 433. This compound is obtained from a commercially available preparation, or is obtained by production through a known method.

Lambda-cyhalothrin is a known compound, and is described in, for example, "The Pesticide Manual—15th edition (published by BCPC); ISBN 978-1-901396-18-8", page 272. This compound is obtained from a commercially available preparation, or is obtained by production through a known method.

Alpha-cypermethrin is a known compound, and is described in, for example, "The Pesticide Manual—15th edition (published by BCPC); ISBN 978-1-901396-18-8", page 277. This compound is obtained from a commercially available preparation, or is obtained by production through a known method.

Bioresmethrin is a known compound, and is described in, for example, "The Pesticide Manual—15th edition (published by BCPC); ISBN 978-1-901396-18-8", page 110. This compound is obtained from a commercially available preparation, or is obtained by production through a known method.

Deltamethrin is a known compound, and is described in, for example, "The Pesticide Manual—15th edition (published by BCPC); ISBN 978-1-901396-18-8", page 313. This compound is obtained from a commercially available preparation, or is obtained by production through a known method.

Bioallethrin is a known compound, and is described in, for example, "The Pesticide Manual—15th edition (published by BCPC); ISBN 978-1-901396-18-8", page 107. This compound is obtained from a commercially available preparation, or is obtained by production through a known method.

Ethofenprox is a known compound, and is described in, for example, "The Pesticide Manual—15th edition (published by BCPC); ISBN 978-1-901396-18-8", page 454. This compound is obtained from a commercially available preparation, or is obtained by production through a known method.

Cypermethrin is a known compound, and is described in, for example, "The Pesticide Manual—15th edition (published by BCPC); ISBN 978-1-901396-18-8", page 277. This compound is obtained from a commercially available preparation, or is obtained by production through a known method.

Zeta-cypermethrin is a known compound, and is described in, for example, "The Pesticide Manual—15th edition (published by BCPC); ISBN 978-1-901396-18-8", page 284. This compound is obtained from a commercially available preparation, or is obtained by production through a known method.

Fenvalerate is a known compound, and is described in, for example, "The Pesticide Manual—15th edition (published by BCPC); ISBN 978-1-901396-18-8", page 494. This compound is obtained from a commercially available preparation, or is obtained by production through a known method.

Cyfluthrin is a known compound, and is described in, for example, "The Pesticide Manual—15th edition (published by BCPC); ISBN 978-1-901396-18-8", page 263. This compound is obtained from a commercially available preparation, or is obtained by production through a known method.

Beta-cyfluthrin is a known compound, and is described in, for example, "The Pesticide Manual—15th edition (published by BCPC); ISBN 978-1-901396-18-8", page 265. This compound is obtained from a commercially available preparation, or is obtained by production through a known method.

Alpha-cypermethrin is a known compound, and is described in, for example, "The Pesticide Manual—15th edition (published by BCPC); ISBN 978-1-901396-18-8", page 279. This compound is obtained from a commercially available preparation, or is obtained by production through a known method.

Tralomethrin is a known compound, and is described in, for example, "The Pesticide Manual—15th edition (published by BCPC); ISBN 978-1-901396-18-8", page 1142. This compound is obtained from a commercially available preparation, or is obtained by production through a known method.

Fluvalinate is a known compound, and is described in, for example, "The Pesticide Manual—15th edition (published by BCPC); ISBN 978-1-901396-18-8", page 1236. This compound is obtained from a commercially available preparation, or is obtained by production through a known method.

Permethrin is a known compound, and is described in, for example, "The Pesticide Manual—15th edition (published by BCPC); ISBN 978-1-901396-18-8", page 879. This compound is obtained from a commercially available preparation, or is obtained by production through a known method.

Flucythrinate is a known compound, and is described in, for example, "The Pesticide Manual—15$^{th}$ edition (published by BCPC); ISBN 978-1-901396-18-8", page 519. This compound is obtained from a commercially available preparation, or is obtained by production through a known method.

The present compound (I) for use in the present invention may be the present composition (I) itself, but is usually formulated into an arbitrary dosage form such as a granule, a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable by mixing the present compound (I) with an appropriate solid carrier or liquid carrier, and adding a surfactant and other formulation additives for a preparation as necessary.

Like the present compound (I), the present compound (II) may be the compound (II) itself, but is usually formulated and used.

In the present invention, a formulation containing the present compound (II), or a formulation containing the present compound (I) and the present compound (II) (hereinafter, referred to as the present formulation in some cases) may be used, or a formulation containing the present compound (I) (hereinafter, referred to as the present formulation (I) in some cases) and a formulation containing the present compound (II) (hereinafter, referred to as the present formulation (II) in some cases) may be used in combination.

In the present invention, when the present formulation (I) and the present formulation (II) are used in combination, the present formulation (I) and the present formulation (II) may be used individually, or may be mixed and used. The dosage forms of the present formulation (I) and the present formulation (II) may be the same, or may be different.

Examples of the solid carrier used upon formulation into a preparation include natural or synthetic minerals such as clay, kaolin, talc, bentonite, sericite, sulfur, active carbon, calcium carbonate, diatomaceous earth, quartz, pumice stone, calcite, meerschaum, dolomite, olivine, pyroxene, amphibole, feldspar, silica, alumina, vermiculite, and perlite; and fine grains of an elastomer, a plastic, a ceramic, a metal, sawdust, corncob, a kernel shell of coconut, a stem of tobacco and the like.

Examples of the liquid carrier include water, xylene, methanol, butanol, pentanol, benzyl alcohol, cyclohexanon, gamma-butyrolactone, N-methyl-pyrrolidone, N-octyl-pyrrolidone, glycoldiacetate, glycols, fatty acid dimethylamides, fatty acids and fatty acid esters. They may be mixed and used.

Examples of the surfactant include common nonionic surfactants, cationic surfactants, anionic surfactants and amphoteric surfactants, and one kind or two or more kinds thereof are used.

Examples of the surfactant include an alkylsulfuric acid salt, an alkylsulfuric acid ester salt, an alkylsulfonic acid salt, an alkylarylsulfonic acid salt, a lignosulfonic acid ester, a naphthalenesulfonic acid salt, a phenolsulfonic acid salt, a dibutylnaphthalenesulfonic acid salt, a fatty alcohol sulfuric acid salt, fatty acid alkyl aryl ethers and polyoxyethylene compounds thereof, polyethylene glycol ethers, polyethylene glycol fatty acid esters, polyhydric alcohol esters, a sugar alcohol derivative and a silicone-based surfactant.

Examples of the other formulation additives for a preparation include an emulsifier, a dispersant, an antifoamer, a stabilizer, an antiseptic and a colorant.

Examples of the preferred emulsifier include a nonionic emulsifier and an anionic emulsifier (e.g. a polyoxyethylene fatty alcohol ether, an alkyl sulfonate and an aryl sulfonate). Examples of the dispersant include a lignin sulfurous acid waste liquid and methyl cellulose.

Examples of the preferred antifoamer include a silicone or magnesium stearate-based antifoamer.

Examples of the colorant include red dyes, blue dyes, green dyes and yellow dyes and the like. Specific examples include Monazole Red, Cyanine Green, Prussian Blue and Brilliant Blue. Particularly, in the case of a granule, it is preferable to add a colorant because the granule is easily identified at the time of application or after application.

Further, for example, glycerin, ethylene glycol and propylene glycol may be added as an antifreezing agent.

When a granule is used in the step C or C' of the present invention, it is applied as such without being diluted.

The granule can be a form such as a fine granule, a macro granule, or a micro granule, by changing the particle size thereof.

In the present invention in which the present compound (II) is used, the content of the present compound (II) in the granule is usually 0.01 to 20% by weight, preferably 0.05 to 10% by weight, further preferably 0.1 to 5% by weight. In the present invention in which the present compound (I) and the present compound (II) are used, the content of each of the present compound (I) and the present compound (II) in the granule is usually 0.01 to 20% by weight, preferably 0.05 to 10% by weight, further preferably 0.1 to 5% by weight.

When a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable is used in the step C or C' of the present invention, an aqueous dispersion or aqueous solution obtained by dispersing or dissolving any of the aforementioned formulations in water is usually applied. The aqueous dispersion or aqueous solution may contain a herbicide, a safener and the like.

The aqueous dispersion of the present compound (I) in the present invention includes a liquid formed by suspending the present compound (I) in water in a solid state, and a liquid formed by emulsifying the present compound (I) in water in a liquid state. The same holds true for the aqueous dispersion of the present compound (II).

In the present invention in which the present compound (II) is used, the application amount of the present compound (II) can be appropriately changed depending on the condition of cultivating corn thereafter and the weather condition, and is usually 5 to 500 g, preferably 10 to 400 g, further preferably 10 to 200 g per hectare of a cultivated land which is seeded with corn. In the present invention in which the present compound (I) and the present compound (II) are used, the application amount of each of the present compound (I) and the compound (II) can be appropriately changed depending on the condition of cultivating corn thereafter and the weather condition, and is usually 5 to 500 g, preferably 10 to 400 g, further preferably 10 to 200 g per hectare of a cultivated land which is seeded with corn.

In the present invention in which the present compound (I) and the present compound (II) are used, the ratio of the application amounts of the present compound (I) and the present compound (II) in the present invention is usually 40:1 to 1:40, preferably 20:1 to 1:20 in terms of a weight ratio.

Usually, the present compound (II), or the present compound (I) and the present compound (II) is/are stored in a tank attached to a tractor body or a seeder pulled with a tractor, and is applied, in linkage with or independently of a vehicle speed, through piping from the tank with movement of the tractor.

In the step C, a granule or micro-granule containing the present compound (II) may be applied before or after seeding, but is preferably applied before seeding, and an aqueous dispersion or aqueous solution of the present compound (II) may be applied before or after seeding, but is preferably applied in parallel to seeding or after seeding, so that the aqueous dispersion or aqueous solution of the present compound (II) is in direct contact with the seed.

When a granule or micro-granule containing the present compound (I) or an aqueous dispersion or aqueous solution of the present compound (II) is used in the step C', the present compound (I) and the present compound (II) are both applied into the furrow, but usually the present compound (I) and the present compound (II) are stored separately in two reservoirs, and each applied into the furrow. The granule or micro-granule containing the present compound (I) may be applied before or after seeding, but is preferably applied before seeding. The aqueous dispersion or aqueous solution of the present compound (II) may be applied before or after seeding, but is preferably applied in parallel to seeding or after seeding, so that the aqueous dispersion or aqueous solution of the present compound (II) is in direct contact with the seed. When the present compound (I) and the present compound (II) are stored separately in two chemical tanks, positions of chemical nozzles are adjusted to perform application orderly so that the compounds do not interfere with each other during application.

Application is performed by a similar operation when the aqueous dispersion or aqueous solution of the present compound (I) and the granule or micro-granule containing the present compound (II) are applied.

When the aqueous dispersion or aqueous solution of the present compound (II), or the aqueous dispersion or aqueous solution of the present compound (I) and the present compound (II) is applied, the type of application is not particularly limited as long as it is capable of application into a furrow, but particularly spraying, dripping or drenching is preferable.

When the type of application is spraying, dripping or drenching, by applying a pressure with a pump or adjusting the opening of a valve of a tank or a hose, the application amount can be adjusted to perform uniform application to a furrow.

The furrow closing part is usually made of rubber or made of cast iron, has a wheel shape, and closes a furrow by gathering together on the side of the furrow with movement of a tractor.

The present invention can reduce damage by harmful organisms in corn cultivation.

In the present invention, the harmful organism refers to pests, weeds and the like.

Specific examples of insect pests which can be controlled by the present invention include insect pests belonging to *Agriotes* spp., *Diabrotica* spp., *Agrotis* spp., *Myzus* spp., *Aphis* spp., *Ostrinia* spp., *Zyginidia* spp., *Sesamia* spp., *Oscinella* spp., *Sitobion* spp., *Scutigerella* spp., *Astylus* spp., *Rhopalosiphum* spp., *Metopolophium* spp., *Melanotus* spp. and *Melolontha* spp., and the present invention is preferably applied as a method for reducing damage by particularly *Agriotes* spp., *Diabrotica* spp., *Agrotis* spp. and *Rhopalosiphum* spp.

The variety of corn, to which the present invention can be applied, is not particularly limited, but application of corn to a hybrid variety is preferable. The hybrid variety is first cross obtained by mating two different type of varieties, and generally has more excellent characteristics than those of both parents.

Corn may be corn to which resistance has been imparted by a genetic engineering technique or a breeding method by mating.

The corn seed used in the present invention is preferably treated with a fungicide, and examples of the fungicide include fludioxonil, metalaxyl, metalaxyl-M, thiuram, triticonazole, carboxin, prochloraz, prothioconazole, sedaxane, penflufen, fluxapyroxad, trifloxystrobin, pyraclostrobin and difenoconazole, and fludioxonil, metalaxyl-M, thiuram, triticonazole, sedaxane, penflufen, and fluxapyroxad are preferable, and fludioxonil, metalaxyl-M and thiuram are more preferable. The corn seed is used after treated with one or more kinds of these fungicides. Alternatively, a commercially available treated seed may be purchased and used.

It is preferable to apply a herbicide to a cultivated land before or after seeding of corn in order to suppress generation of weeds during a cultivation term of corn, and examples of the herbicide include mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluroxypyr, pethoxamid, flumioxazin, thiencarbazone-methyl, iodosulfuron-methyl-sodium salt, prosulfuron, topramezone, metosulam, cycloxydim, aclonifen, dimethenamid, florasulam, clopyralid, flazasulfuron, imazamox, MCPA, 2,4-D, linuron, propisochlor, thifensulfuron methyl and tritosulfuron; preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluroxypyr, pethoxamid, flumioxazin, thiencarbazone-methyl, iodosulfuron-methyl-sodium salt, prosulfuron, topramezone, metosulam, cycloxydim and aclonifen; more preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluroxypyr, pethoxamid, flumioxazin, thiencarbazone-methyl and iodosulfuron-methyl-sodium salt. Usually, one or more of these herbicides are applied. When two or more thereof are applied, they may be applied simultaneously, or they may be applied separately. When they are applied separately, they may be applied on the same day, or on another day.

These herbicides may be applied by, if necessary, mixing with a safener. Examples of the safener include isoxadifen-ethyl, furilazole, dichlormid, benoxacor and cyprosulfamide.

EXAMPLES

Next the present invention will be further described byway of the following examples, but the present invention is not limited to these examples.

Example 1

A land was ditched at intervals of 75 cm to a depth of 3 cm from the soil surface, a predetermined amount of a mixed liquid of a water-diluted liquid of a clothianidin water disperscible granule (using a 50% water disperscible granule, trade name: DANTOP, manufactured by Philagro) and a water-diluted liquid of an esfenvalerate emulsifiable concentrate (using 50 g/L of an EC preparation, trade name: Sumialpha 5EC, manufactured by Philagro) or a mixed liquid of a water-diluted liquid of a clothianidin water disperscible granule (using a 50% water disperscible granule, trade name: DANTOP) and a water-diluted liquid of a lambda-cyhalothrin SC (using 100 g/L of a SC preparation, trade name: KAPATE ZEON, manufactured by SYNGENTA) was prepared so that the applied amount of an effective component was the amount described in Table 1, and the furrow was spray-treated with the mixed liquid at a spray amount of 100 L/ha. Then, the furrow was seeded with corn (*Zea Mays*, variety name: Kubrik) at intervals of 17 cm, and a soil on the side of the furrow was gathered together to close the furrow. A seeding density of corn was 78000 seeds/ha. They were defined as example sections 1 and 2.

For comparison, a non-treatment section, which was seeded with corn in the same manner as in the example sections except that a treatment with a chemical was not performed, was provided.

In any section, four places were arranged by a randomized block method, with one place having an area of 54 m² (18 m×3 m).

34 days after the treatment with a chemical, the total number of plants of corn and the number of plants of corn damaged by *Agriotes sotdidus* in each of the example sections 1 and 2 and the non-treatment section were investigated, a damage plant rate was calculated in accordance with the following equation, and then an average damage plants rate of the four investigation sections was determined.

Damage plant rate (%)={(number of plants of corn damaged)/(total number of plants of corn)}×100

The results are shown in Table 1.

TABLE 1

| | Application amount of clothianidin (g/ha) | Name and application amount (g/ha) of the present compound (II) | Damage plant rate (%) |
|---|---|---|---|
| Example section 1 | 25 | Esfenvalerate 20 | 2.3 |
| Example section 2 | 25 | Lambda-cyhalothrin 7.5 | 1.7 |
| Non-treatment section | 0 | 0 | 34.6 |

Example 2

In a glass bottle having a volume of 10 ml, 10 mg of esfenvalerate was dissolved in 1.8 ml of acetone, and 2 g of diatomaceous earth fine grains (trade name: ISOLITE CG, manufactured by ISOLITE INSULATING PRODUCTS CO., LTD.) was added to the glass bottle, and the glass bottle was strongly shaken to obtain a 0.5% esfenvalerate granule.

A clothianidin granule (using a 0.7% granule, trade name: Dantotsu Granule, manufactured by Sumitomo Chemical Company, Limited), a thiamethoxam granule (using a 0.5% granule, trade name: Actara Granule 5, manufactured by Syngenta Japan K. K.), an imidacloprid granule (using a 1.0% granule, trade name: Admirer 1 Granule, manufactured by Bayer CropScience K.K.) or a thiacloprid granule (using a 1.0% granule, trade name: BARIARD Box Granule, manufactured by Nihon Nohyaku Co., Ltd.) and a tefluthrin granule (using a 0.5% granule, trade name: Force Granule, manufactured by Syngenta Japan K.K.) or the above-mentioned esfenvalerate were mixed in the combination described in Table 2.

A plastic cup (diameter 7 cm) having a volume of 390 ml was filled with a soil, a furrow was formed to a depth of 3 cm from the soil surface, the prepared mixed granule was, respectively, applied in the chemical amount described in Table 2, the furrow was seeded with corn (variety name: Pioneer 32K61, hybrid variety) in an amount of one grain per cup, and a soil on the side of the furrow was gathered together to close the furrow. Corn was grown in a usual green house.

10 days after seeding of corn, 10 insects of *Rhopalosiphum padi* were released in each cup. This is called a treatment section.

On the other hand, except that a mixed granule was not applied, corn was grown in a usual green house in the same manner as in the treatment section, and 10 insects of *Rhopalosiphum padi* were released. This is called a non-chemical-treatment section.

3 days after insect releasing, the number of *Rhopalosiphum padi* was investigated, and a preventive value was calculated using the following equation. The results are shown in Table 2.

preventive value=100×(A−B)/A

A: number of insects during investigation of non-chemical-treatment section

B: number of insects during investigation of treatment section

TABLE 2

| | The present compound (I) | The present compound (II) | Preventive value |
|---|---|---|---|
| Example section 3 | Clothianidin 25 g a.i./ha | Tefluthrin 25 g a.i./ha | 100 |
| Example section 4 | Clothianidin 25 g a.i./ha | Tefluthrin 100 g a.i./ha | 100 |
| Example section 5 | Clothianidin 25 g a.i./ha | Tefluthrin 150 g a.i./ha | 100 |
| Example section 6 | Imidacloprid 100 g a.i./ha | Tefluthrin 25 g a.i./ha | 100 |
| Example section 7 | Thiamethoxam 100 g a.i./ha | Tefluthrin 50 g a.i./ha | 100 |
| Example section 8 | Thiamethoxam 150 g a.i./ha | Esfenvalerate 25 g a.i./ha | 100 |
| Example section 9 | Thiacloprid 150 g a.i./ha | Tefluthrin 25 g a.i./ha | 100 |

Example 3

Aqueous solutions of a thiamethoxam water soluble granule (using a 10.0% preparation, trade name: Actara Water Soluble Granule, manufactured by Syngenta Japan K.K.), an imidacloprid water dispersible granule (using a 50.0% preparation, trade name: Admire Water dispersible Granule, manufactured by Bayer CropScience K.K.) and a thiacloprid water dispersible granule (using a 30.0% preparation, trade name: Bariard Water Dispersible Granule, manufactured by Bayer CropScience K.K.) and aqueous solutions of an esfenvalerate emulsifiable concentrate (using 50 g/L of an EC preparation, trade name: Sumialpha 5EC, manufactured by Philagro), a lambda-cyhalothrin emulsifiable concentrate (using 25 g/L of an EC preparation, trade name: KARATE 2.5EC, manufactured by SYNGENTA) and a cypermethrin emulsifiable concentrate (using 50 g/L of an EC preparation, trade name: Cymbush 5EC, manufactured by SYNGENTA)

were mixed so as to achieve the combination and chemical amount described in Table 3, thereby preparing a liquid containing the chemicals.

A plastic cup (diameter 7 cm) having a volume of 390 ml was filled with a soil, a furrow was formed to a depth of 3 cm from the soil surface, the prepared liquid containing chemical was, respectively, applied in the chemical amount described in Table 3, the furrow was seeded with corn (variety name: Pioneer, hybrid variety) in an amount of one grain per cup, and a soil on the side of the furrow was gathered together to close the furrow. Corn was grown in a usual green house.

10 days after seeding of corn, 10 insects of *Rhopalosiphum padi* were released in each cup. This is called a treatment section.

On the other hand, except that a liquid containing the chemical was not applied, corn was grown in a usual green house in the same manner as in the treatment section, and 10 insects of *Rhopalosiphum padi* were released. This is called a non-chemical-treatment section.

3 days after insect releasing, the number of *Rhopalosiphum padi* was investigated, and a preventive value was calculated using the following equation. The results are shown in Table 3.

preventive value=100×(A−B)/A

A: number of insects during investigation of non-chemical-treatment section
B: number of insects during investigation of treatment section

TABLE 3

| | The present compound (I) | The present compound (II) | Preventive value |
|---|---|---|---|
| Example section 10 | Imidacloprid 20 g a.i./ha | Esfenvalerate 200 g a.i./ha | 100 |
| Example section 11 | Imidacloprid 200 g a.i./ha | Lambda-cyhalothrin 20 g a.i./ha | 100 |
| Example section 12 | Imidacloprid 20 g a.i./ha | Cypermethrin 200 g a.i./ha | 100 |
| Example section 13 | Thiamethoxam 20 g a.i./ha | Lambda-cyhalothrin 200 g a.i./ha | 100 |
| Example section 14 | Thiamethoxam 100 g a.i./ha | Cypermethrin 50 g a.i./ha | 100 |
| Example section 15 | Thiacloprid 200 g a.i./ha | Cypermethrin 20 g a.i./ha | 100 |

Example 4

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener), a cultivated land is ditched at intervals of 75 cm to a depth of 5 cm from the soil surface, and a mixed granule of clothianidin and tefluthrin is applied to the furrow so as to achieve an application amount of 30 g/ha for clothianidin and 50 g/ha for tefluthrin. After application, the furrow is seeded with corn (*Zea Mays*: hybrid variety). The furrow is seeded at intervals of 20 cm using, as a seed of corn, one treated with thiuram. A seeding density of corn is 70000 seeds/ha. After the furrow is seeded with corn, a soil on the side of the furrow is gathered together to close the furrow. This is called a treatment section.

For comparison, the furrow is seeded with corn by the operation same as that in the treatment section except that clothianidin and tefluthrin are not applied. This is called a non-treatment section.

In any section, four places are arranged by a randomized block method, with one place having an area of 45 m² (15 m×3 m).

17 days after application of clothianidin and tefluthrin, the number of plants of corn germinated is investigated, with central two rows of four rows of seeded furrows as an investigation section, for the treatment section and the non-treatment section. 165 days after application of clothianidin and tefluthrin, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

Example 5

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener) equipped with a power sprayer, a cultivated land is ditched at intervals of 75 cm to a depth of 3 cm from the soil surface, and a tefluthrin granule is applied to the furrow such that the application amount of tefluthrin is 75 g/ha. After application, the furrow is seeded with corn (*Zea Mays*: hybrid variety). The furrow is seeded at intervals of 20 cm using, as a seed of corn, one treated with thiuram. A seeding density of corn is 70000 seeds/ha. In parallel with seeding of corn, an aqueous suspension of imidacloprid is applied to the furrow such that the chemical is in direct contact with the seed. The furrow is spray-treated at 150 L/ha so that the application amount of imidacloprid is 100 g/ha, and then a soil on the side of the furrow is gathered together to close the furrow. This is called a treatment section.

For comparison, the furrow is seeded with corn by the operation same as that in the treatment section except that tefluthrin and imidacloprid are not applied. This is called a non-treatment section.

In any section, four places are arranged by a randomized block method, with one place having an area of 45 m² (15 m×3 m).

17 days after application of tefluthrin and imidacloprid, the number of plants of corn germinated is investigated, with central two rows of four rows of seeded furrows as an investigation section, for the treatment section and the non-treatment section. 165 days after application of tefluthrin and imidacloprid, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

Example 6

Ammonium phosphate (N:P:K=12:52:0) and urea (N:P:K=46:0:0), each of which being a fertilizer, are applied to the soil surface of a cultivated land at 100 kg/ha and 260 kg/ha, respectively, and the cultivated land is then plowed.

In order to prevent generation of weeds, 28 days after fertilization, the whole cultivated land is spray-treated with a mixed agent (using 610 g/kg water dispersible granule, trade name: MaisTer, manufactured by Bayer CropScience) of foramsulfuron and an iodosulfuron-methyl-sodium salt, each of which being a herbicide, and a safener, isoxadifen-ethyl, at 0.15 L/ha in terms of an application amount of the preparation.

3 days after application of the preparation, using a pneumatic seeder (disk furrow opener) equipped with a power sprayer, a cultivated land is ditched at intervals of 75 cm to a depth of 4 cm from the soil surface, and the furrow is seeded with corn (*Zea Mays*; hybrid variety). The cultivated land is seeded at intervals of 20 cm using, as a corn seed, one treated with a mixed agent of metalaxyl-M and fludioxonil (trade name: Maxim XL, manufactured by Syngenta). A seeding density of corn is 66667 seeds/ha. Then, the furrow is spray-treated with a mixed aqueous suspension of tefluthrin and thiamethoxam at 125 L/ha so that the application amount is 50 g/ha for tefluthrin and 50 g/ha for thiamethoxam. This is called a treatment section.

For comparison, the furrow is seeded with corn by the operation same as that in the treatment section except that tefluthrin and thiamethoxam are not applied. This is called a non-treatment section.

In any section, four places are arranged by a randomized block method, with one place having an area of 45 m² (15 m×3 m).

17 days after application of tefluthrin and thiamethoxam, the number of plants of corn germinated is investigated, with central two rows of four rows of seeded furrows as an investigation section, for the treatment section and the non-treatment section.

165 days after application of tefluthrin and thiamethoxam, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

Example 7

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, at 150 L/ha so that the application amounts of thiencarbazone-methyl and isoxaflutole are 9.2 g/ha and 23 g/ha.

21 days after fertilization, using a pneumatic seeder (disk furrow opener), a cultivated land is ditched at intervals of 75 cm to a depth of 5 cm from the soil surface, and a mixed granule of clothianidin and tefluthrin is applied to the furrow so as to achieve an application amount of 30 g/ha for clothianidin and 50 g/ha for tefluthrin. After application, the furrow is seeded with corn (*Zea Mays*: hybrid variety). The furrow is seeded at intervals of 20 cm using, as a seed of corn, one treated with thiuram and cyprosulfamide which is a safener. A seeding density of corn is 70000 seeds/ha. After the furrow is seeded with corn, a soil on the side of the furrow is gathered together to close the furrow. This is called a treatment section.

For comparison, the furrow is seeded with corn by the operation same as that in the treatment section except that clothianidin and tefluthrin are not applied. This is called a non-treatment section.

In any section, four places are arranged by a randomized block method, with one place having an area of 45 m² (15 m×3 m).

17 days after application of clothianidin and tefluthrin, the number of plants of corn germinated is investigated, with central two rows of four rows of seeded furrows as an investigation section, for the treatment section and the non-treatment section. 165 days after application of clothianidin and tefluthrin, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

Example 8

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, at 150 L/ha so that the application amounts of thiencarbazone-methyl and isoxaflutole are 9.2 g/ha and 23 g/ha.

21 days after fertilization, using a pneumatic seeder (disk furrow opener) equipped with a power sprayer, a cultivated land is ditched at intervals of 75 cm to a depth of 3 cm from the soil surface, and a tefluthrin granule is applied to the furrow such that the application amount of tefluthrin is 75 g/ha. After application, the furrow is seeded with corn (*Zea Mays*: hybrid variety). The furrow is seeded at intervals of 20 cm using, as a seed of corn, one treated with thiuram. A seeding density of corn is 70000 seeds/ha. In parallel with seeding of corn, an aqueous suspension of imidacloprid and cyprosulfamide which is a safener is applied to the furrow such that the chemical is in direct contact with the seed. The furrow is spray-treated at 150 L/ha so that the application amounts of imidacloprid and cyprosulfamide are 100 g/ha and 15 g/ha, and then a soil on the side of the furrow is gathered together to close the furrow. This is called a treatment section.

For comparison, the furrow is seeded with corn by the operation same as that in the treatment section except that tefluthrin and imidacloprid are not applied. This is called a non-treatment section.

In any section, four places are arranged by a randomized block method, with one place having an area of 45 $m^2$ (15 m×3 m).

17 days after application of tefluthrin and imidacloprid, the number of plants of corn germinated is investigated, with central two rows of four rows of seeded furrows as an investigation section, for the treatment section and the non-treatment section. 165 days after application of tefluthrin and imidacloprid, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/(plant number of corn germinated)]×100

As a result, the treatment section shows a low lodge rate as compared to the non-treatment section, and is found to have reduced damage by harmful organisms in corn cultivation.

Example 9

A land was ditched at intervals of 80 cm, a predetermined amount of a water-diluted liquid of an esfenvalerate emulsifiable concentrate (using 25 g/L of an EC preparation, trade name: Sumialpha 2.5 EC, manufactured by Philagro) or a water-diluted liquid of a lambda-cyhalothrin SC (using 100 g/L of a SC preparation, trade name: KAPATE ZEON, manufactured by SYNGENTA) was prepared so that the applied amount of an effective component was the amount described in Table 4, and the furrow was spray-treated with the liquid at a spray amount of 100 L/ha. Then, the furrow was seeded with corn (*Zea Mays*, variety name: Kubrik), and a soil on the side of the furrow was gathered together to close the furrow. A seeding density of corn was 87500 seeds/ha. They were defined as example sections 16 and 17.

For comparison, a non-treatment section, which was seeded with corn in the same manner as in the example sections except that a treatment with a chemical was not performed, was provided.

In any section, four places were arranged by a randomized block method, with one place having an area of 38.4 $m^2$ (12 m×3.2 m) and other three places having an 32 $m^2$ (10 m×3.2 m).

34 days after the treatment with a chemical, the number of plants of corn grown in each of the example sections 16 and 17 and the non-treatment section were investigated, a mortality of plants of corn died because of the damage by *Agriotes* spp. was calculated in accordance with the following equation, and then an average mortality of the four investigation sections was determined.

Mortality (%)={(number of corns seeded)−(number of plants of corn grown)/(number of corns seeded)}×100

The results are shown in Table 4.

TABLE 4

| | Name and application amount (g/ha) of the present compound (II) | Average mortality (%) |
|---|---|---|
| Example section 16 | Esfenvalerate 50 | 4.85 |
| Example section 17 | Lambda-cyhalothrin 50 | 3.35 |
| Non-treatment section | 0 | 16.35 |

Example 10

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener), a cultivated land is ditched at intervals of 75 cm to a depth of 5 cm from the soil surface, and a water-diluted liquid of an esfenvalerate emulsifiable concentrate (using 25 g/L of an EC preparation, trade name: Sumialpha 2.5 EC, manufactured by Philagro) is applied to the furrow so as to achieve an application amount of 100 g/ha for esfenvalerate. After application, the furrow is seeded with corn (*Zea Mays*: hybrid variety). The furrow is seeded at intervals of 20 cm using, as a seed of corn, one treated with thiuram. A seeding density of corn is 70000 seeds/ha. After the furrow is seeded with corn, a soil on the side of the furrow is gathered together to close the furrow. This is called a treatment section.

For comparison, the furrow is seeded with corn by the operation same as that in the treatment section except that esfenvalerate is not applied. This is called a non-treatment section.

In any section, four places are arranged by a randomized block method, with one place having an area of 45 $m^2$ (15 m×3 m). 17 days after application of esfenvalerate, the number of plants of corn germinated is investigated, with central two rows of four rows of seeded furrows as an investigation section, for the treatment section and the non-treatment section. 165 days after application of esfenvalerate, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

Example 11

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid containing thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively.

21 days after fertilization, using a pneumatic seeder (disk furrow opener), a cultivated land is ditched at intervals of 75 cm to a depth of 5 cm from the soil surface, and a water-diluted liquid of a lambda-cyhalothrin SC (using 100 g/L of a SC preparation, trade name: KAPATE ZEON, manufactured by SYNGENTA) is applied to the furrow such that the application amount of lambda-cyhalothrin is 100 g/ha. After application, the furrow is seeded with corn (*Zea Mays*: hybrid variety). The furrow is seeded at intervals of 20 cm using, as a seed of corn, one treated with thiuram. A seeding density of corn is 70000 seeds/ha. After the furrow is seeded with corn, a soil on the side of the furrow is gathered together to close the furrow. This is called a treatment section.

For comparison, the furrow is seeded with corn by the operation same as that in the treatment section except that lambda-cyhalothrin is not applied. This is called a non-treatment section.

In any section, four places are arranged by a randomized block method, with one place having an area of 45 m² (15 m×3 m).

17 days after application of lambda-cyhalothrin, the number of plants of corn germinated is investigated, with central two rows of four rows of seeded furrows as an investigation section, for the treatment section and the non-treatment section. 165 days after application of lambda-cyhalothrin, the number of plants of corn lodged due to damage by *Diabrotica virgifera virgifera* and *Agriotes lineatus* in the furrows of the treatment section and the non-treatment section, for which the number of plants of corn germinated is investigated, is investigated, a lodge rate is calculated in accordance with the following equation, and then an average lodge rate for the four investigation sections is determined.

Lodge rate (%)=[(plant number of corn lodged)/
(plant number of corn germinated)]×100

As a result, the treatment section shows a low lodge rate as compared to the non-treatment section, and is found to have reduced damage by harmful organisms in corn cultivation.

The invention claimed is:

1. A method for reducing damage by harmful organisms in corn cultivation, the method comprising the steps of:
A) making a furrow in a cultivated land; B) seeding with corn the furrow formed in the foregoing step; C) applying to the furrow one or more selected from the below-mentioned compound group (II); and D) closing the furrow,
(compound group (II): group consisting of bifenthrin, bioresmethrin, bioallethrin, ethofenprox, fenpropathrin, alpha-cypermethrin, zeta-cypermethrin, fenvalerate, beta-cyfluthrin, alpha-cypermethrin, tralomethrin, fluvalinate, permethrin, lambda-cyhalothrin, flucythrinate and tefluthrin),
wherein the step of applying one or more selected from the compound group (II) is a step of applying a composition containing one or more selected from the compound group (II), and
wherein the composition containing one or more selected from the compound group (II) is an aqueous dispersion or aqueous solution containing one or more selected from the compound group (II).

2. The method according claim 1, wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (II).

3. The method according to claim 1, wherein the land is ditched to a depth of 1 to 10 cm.

4. The method according to claim 1, wherein making the furrow is performed using a disk furrow opener.

5. The method according to claim 1, wherein seeding is performed using a pneumatic seeder.

* * * * *